United States Patent
Woods et al.

(10) Patent No.: US 6,627,762 B1
(45) Date of Patent: Sep. 30, 2003

(54) ACETAL AND HEMIACETAL ESTER LINKED PROPYLENE CARBONATE FUNCTIONAL (METH)ACRYLIC ESTERS AND METHOD OF MAKING SAME

(76) Inventors: John G. Woods, 5 Beechwood Rd., Farmington, CT (US) 06032; Susanne D. Morrill, 66 Brunswick Ave., West Hartford, CT (US) 06107

( * ) Notice: Subject to any disclaimer, the term of this patent is extended or adjusted under 35 U.S.C. 154(b) by 0 days.

(21) Appl. No.: 10/277,988

(22) Filed: Oct. 23, 2002

(51) Int. Cl.$^7$ ................ C07D 317/36; C08F 124/00
(52) U.S. Cl. ........................ 549/229; 526/269
(58) Field of Search ............ 549/229; 526/269

(56) References Cited

U.S. PATENT DOCUMENTS

| | | | |
|---|---|---|---|
| 3,218,305 A | 11/1965 | Krieble | 260/89.5 |
| 4,058,400 A | 11/1977 | Crivello | 96/86 P |
| 4,058,401 A | 11/1977 | Crivello | 96/115 R |
| 4,180,640 A | 12/1979 | Melody et al. | 526/323.1 |
| 4,219,654 A | 8/1980 | Crivello | 546/342 |
| 4,287,330 A | 9/1981 | Rich | 526/270 |
| 4,321,349 A | 3/1982 | Rich | 526/270 |
| 4,808,638 A | 2/1989 | Steinkraus et al. | 522/24 |
| 5,079,378 A | 1/1992 | Crivello | 556/64 |
| 5,621,119 A * | 4/1997 | Podszun et al. | 549/229 |
| 6,001,535 A * | 12/1999 | Podszun et al. | 430/285.1 |

FOREIGN PATENT DOCUMENTS

| | | | |
|---|---|---|---|
| EP | 0 001 088 | 6/1978 | C08F/20/28 |
| EP | 0 667 560 | 1/1995 | G03F/7/027 |
| WO | 92/04383 | 3/1992 | C08F/2/50 |
| WO | 00/40663 | 7/2000 | C09J/4/00 |
| WO | 02/42383 | 5/2002 | C09D/4/00 |

OTHER PUBLICATIONS

Decker, C. et al., *Macromol. Chen. Rapid Commun. 11*, pp. 159–167, ( 1990).
Decker, C. et al., "Radiation Curing in Polymer Science & Technology", Cpt. 2 of vol. III, Fouassier et al. Eds., Elsevier Appied Science, NY (1993).
Jansen et al. Eds., "Polymer Preprints", 42(2), 769 (2001).

* cited by examiner

*Primary Examiner*—Bernard Dentz
(74) *Attorney, Agent, or Firm*—Steven C. Bauman

(57) ABSTRACT

Compounds of the formula:

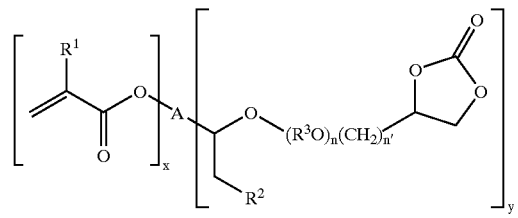

wherein
  $R^1$ is H or methyl,
  $R^2$ is H or alkyl,
  $R^3$ is $C_2$–$C_4$ alkylene,
  n is 0–4,
  n' is 1–4,
  x is one or more,
  y is one or more,
  x+y=z, and
  A is a z-valent organic group linked to the group or groups on the left thereof through a carbon atom and is linked to the group or groups on the right thereof through an ether or ester oxygen atom, or, provided that x and y are both 1, a direct bond.

29 Claims, No Drawings

ACETAL AND HEMIACETAL ESTER LINKED PROPYLENE CARBONATE FUNCTIONAL (METH)ACRYLIC ESTERS AND METHOD OF MAKING SAME

BACKGROUND OF THE INVENTION (Meth)acrylate ester compounds having cyclic propylene carbonate groups are described in Decker, C., et al, *Makromol. Chem, Rapid Commun*, 11, 159–167 (1990); Decker, C., et al, Cpt. 2 of Vol. III "Radiation Curing in Polymer Science and Technology," Fouassier et al, eds, Elsevier Applied Science, NY (1993); Jansen, et al, Polymer Preprints, 42(2), 769 (2001); U.S. Pat. No. 5,621,119; U.S. Pat. No. 6,001,535; European Patent No. EP 0 001 088; European Pat. No. EP 0 667 560; and International Patent Publication No. WO 02/42383. Such compounds have advantages in radiation curing compositions, for instance, for their high cure rates and improved hardness and flexibility properties.

A variety of different linking structures between the (meth)acrylate ester group and the cyclic propylene carbonate groups are described in the documents listed above. However, it has not previously been proposed to prepare such compounds with acetal or hemiacetal ester moieties in the linking structure.

SUMMARY OF THE INVENTION

The present invention is directed to novel acetal or hemiacetal ester linked propylene carbonate functional (meth)acrylic esters, and to methods for their synthesis.

The inventive compounds are characterized by the formula:

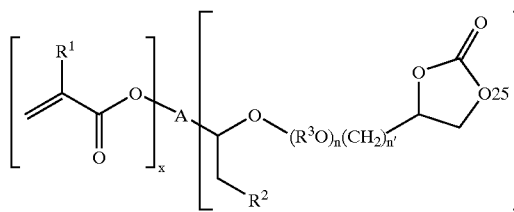

(I)

where $R^1$ is H or methyl, $R^2$ is H or alkyl, each $R^3$, independently, is a $C_2$–$C_4$ alkylene, n is 0–4, n' is 1–4, x is one or more, y is one or more, x+y=z, and A is a z-valent organic group linked to the group(s) on the left thereof through a carbon atom thereof and linked to the group(s) on the right thereof through an ether or ester oxygen atom, or, provided that x and y are both 1, is a direct bond.

The inventive compounds may be readily synthesized by reaction of certain alk-1-enyl alkylene cyclocarbonate ethers and known (meth)acrylic carboxylic acids or hydroxy functional (meth)acrylic esters. In addition to providing compounds having a single (meth)acrylate and a plurality of cyclic propylene carbonate groups, the method is readily adaptable to preparation of compounds having a each of these functionalities, but with one or the other, or both, being present in a plurality.

DETAILED DESCRIPTION OF THE INVENTION

All published documents, including all U.S. patent documents, mentioned anywhere in this application are hereby expressly incorporated herein by reference in their entirety. Any copending patent applications, mentioned anywhere in this application are also hereby expressly incorporated herein by reference in their entirety.

A. Monomer Compounds

Alk-1-enyl alkylene cyclocarbonate ethers of the formula:

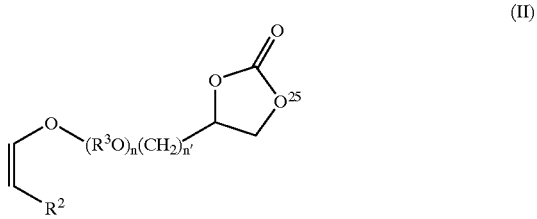

(II)

where $R^2$, $R^3$, n and n' are as previously defined, are known, for instance from WO 92/04383. Such alk-1-enyl ethers may be reacted with (meth)acrylic carboxylic acids or hydroxy functional (meth)acrylic esters to produce the compounds of the invention.

In formula I above, the z-valent organic group A may be for instance an alkylene group, such as ethylene, propylene and butylene; a group of the formula —$(R^3O)_{n''}$—, where $R^3$ is as previously defined and n" is as defined for n; an alkyleneacetyloxy group. The group A may also be a residue of any other partially (meth)acrylated polyol, for instance the glycerol residue of glyceryl monoacrylate or of glyceryl diacrylate.

Examples of suitable $R^2$ groups include H, and methyl, ethyl, n-propyl, isopropyl, butyl, cyclohexyl, hexyl, phenyl, octyl, 2-ethylhexyl, decyl, lauryl, cetyl and octadecyl. In some embodiments $R^2$ may be H or an alkyl group of 1–10 carbon atoms, especially H (i.e. a vinyl ether), or methyl (i.e. a propenyl ether).

Examples of $R^3$ groups include ethylene, 1,2-propylene, 1,3-propylene, 1,4-butylene and 1,2-butylene.

Specific useful ether compounds which may be employed in such synthesis reactions are prop-1-enyl propylene carbonate (PEPC), and the vinyloxyethyl ether of propylene carbonate.

Useful (meth)acrylic carboxylic acids which may be employed in such synthesis reactions include acrylic acid, methacrylic acid, B-carboxyethyl acrylate and B-carboxyethyl methacrylate.

Useful (meth)acrylic hydroxy esters which may be employed in such synthesis reactions are partially (meth)acrylated diols and polyols. Examples of such compounds include hydroxyethyl acrylate, hydroxyethyl methacrylate, hydroxypropyl acrylate, hydroxypropyl methacrylate, glyceryl monomethacrylate, glyceryl monoacrylate, glyceryl dimethacrylate, glyceryl diacrylate, trimethylol propane monomethacrylate, trimethylol propane monomethacrylate, trimethylol diacrylate, trimethylol propane dimethacrylate; pentaerythritol tri(meth)acrylate, pentaerythritol di(meth) acrylate, pentaerythritol mono(meth)acrylate, sorbitol penta (meth)acrylate, sorbitol tetra(meth)acrylate, sorbitol tri(meth)acrylate, sorbitol di(meth)acrylate, sorbitol mono(meth)acrylate, hydroxy functional saccharide (meth)acrylates, diethylene glycol mono(meth)acrylate, poly(ethylene glycol) mono(meth)acrylate, dipropylene glycol mono(meth)acrylate; poly(propylene glycol) mono(meth)acrylate, and the like.

The reaction of the alk-1-enyl alkylene cyclocarbonate ethers with the (meth)acrylic carboxylic acids and/or (meth)acrylic hydroxy esters is a simple thermally driven addition across the alk-1-enyl double bond. Addition of a hydroxyalkyl (meth)acrylate to a compound of formula II above, produces an acetal linked propylene carbonate functional (meth)acrylic ester, whereas addition of a (meth)acrylic acid compound produces a hemiacetal linked propylene carbonate functional (meth)acrylic ester. The addition reactions are run at elevated temperature, suitably a temperature range 20–120° C., preferably below 100° C. and above 50° C., and especially at about 70–90° C. for a time of 1–12 hours. Advantageously, the hydroxy ester or carboxylic acid is added to the compound of formula II incrementally. Typically a stabilizer is added to prevent premature polymerization. In certain cases it may be advantageous to employ an acidic catalyst such as para-toluene sulfonic acid or phosphoric acid to increase the reaction rates or to drive the reaction to completion.

In general, a suitable work-up procedure involves washing or treating the crude reaction mixture with sodium bicarbonate solution to remove residual acids (reagent and catalyst) if present, followed by washing with water to remove ionic impurities, drying with a suitable desiccant and filtering to remove insoluble particulate contaminants. In certain cases it may be desirable to vacuum strip the crude product and in some cases to distill or precipitate the monomers from blends of solvents and non-solvents. In other cases, chromatographic separation may be appropriate, particularly where isolation of highly purified material is required.

In an alternate synthesis, alk-1-enyl alkyleneepoxy ether compounds, for instance vinyl glycidyl ether or 1-propenyl glycidyl ether, may be first reacted with a hydroxyalkyl (meth)acrylate or a (meth)acrylic acid compound, to produce an acetal linked epoxy functional (meth)acrylic ester or a hemiacetal linked epoxy functional (meth)acrylic ester, respectively. Such products may then be reacted with carbon dioxide to form the desired propylene carbonate compound of the invention.

The inventive compounds are illustrated by the following:

Reaction product of propylene ether of propylene carbonate (PEPC) and acrylic acid:

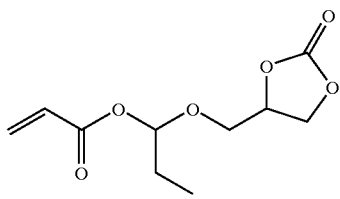

Reaction product of vinyloxyethyl ether of propylene carbonate and acrylic acid

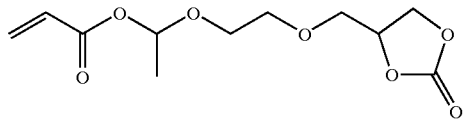

Reaction product of PEPC and β-carboxyethyl acrylate:

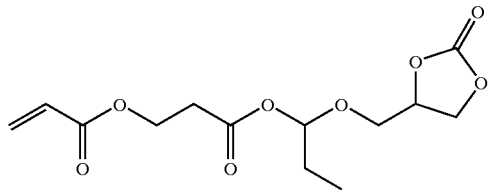

Reaction product of vinyloxyethyl ether of propylene carbonate and 2-hydroxyethyl acrylate:

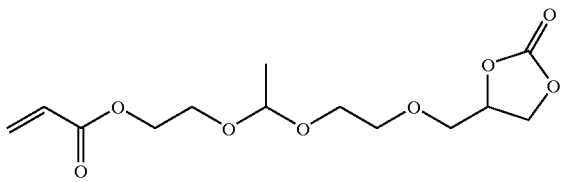

Reaction product of PEPC and 2-hydroxyethyl acrylate:

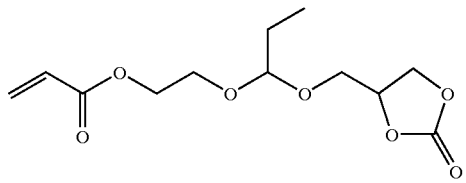

Reaction product of PEPC and glycerol dimethacrylate:

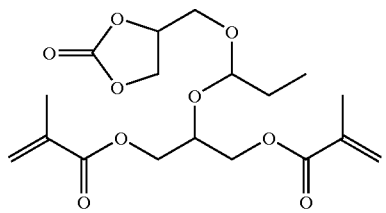

Reaction product of PEPC and glycerol monomethacrylate:

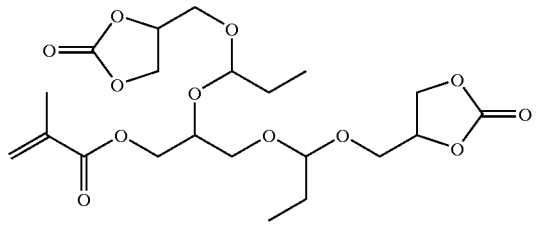

and

Reaction product of 3-(2-vinyloxyethoxy)propylene-1,2-carbonate and acrylic acid:

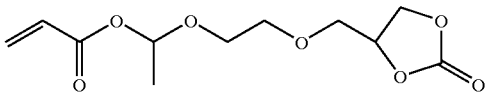

The acetal-linked propylene carbonate functional (meth)acrylic ester compounds of the invention may be used as reactive diluents in conventional polymer-forming compositions based on free-radically polymerizable ethylenically unsaturated compounds. They are low viscosity monomers with excellent solubilizing properties and very high reactivity in free radical polymerization and copolymerization reactions. They may be employed as neat monomers (i.e. 100%) but more typically they may be used to modify (meth)acrylate-based formulations as additives that are effective at levels ranging from about 1% to about 90% or more, typically at levels ranging from about 5% to about 50% by weight of the total composition. The amount employed will depend on the particular formulation used, the desired rheology and reactivity of the modified formulation and on the final properties of the cured material.

The new monomers are compatible with radiation, anaerobic and 2-part structural adhesive cure systems. Although mono-functional in (meth)acrylate, the monomers cure to give crosslinked, insoluble polymers and copolymers.

B. Curable Compositions

As mentioned, curable formulations of the invention will typically include one or more other free-radically polymerizable ethylenically unsaturated compounds, in addition to the inventive monomers. Such compounds include a wide variety of materials represented by $(H_2C=CR^4C(=O)Q)_n R^5$, where $R^4$ may be hydrogen, halogen or alkyl of 1 to about 4 carbon atoms, Q is O, NH or $NCH_3$, n is a positive number of at least 1 and $R^5$ is any n-valent organic group. $R^5$ may be, for instance, alkyl, cycloalkyl, alkenyl, cycloalkenyl, alkaryl, aralkyl or aryl groups of 1 to about 16 carbon atoms, any of which may be optionally substituted or interrupted as the case may be with silane, silicon, oxygen, halogen, carbonyl, hydroxyl, ester, carboxylic acid, urea, urethane, carbamate, amine, amide, sulfur, sulfonate, sulfone and the like.

The inventive monomer compounds may be employed in an amount of about 1% to about 99% by weight of the composition, more typically from about 10% to about 70%, and especially from 20% to about 50% by weight of the composition. The other free-radically polymerizable ethylenically unsaturated compounds may be employed in an amount of about 1% to about 99% by weight of the composition, more typically from about 5% to about 85%, and especially from 10% to about 60% by weight of the composition.

Suitable (meth)acrylate monomers which may be included as other free-radically polymerizable ethylenically unsaturated compounds in the compositions of the invention are, for instance, mono, di, or poly(meth)acrylate compounds, including various prepolymer compounds such as urethane acrylates and epoxy acrylates, and oligomers. Examples include β-carboxyethyl acrylate, isopropyl acrylate, ethyl acrylate, propyl acrylate, n-octyl acrylate, n-decyl acrylate, cyclohexyl acrylate, tetrahydrofurfuryl acrylate, 2-ethylhexyl acrylate, ethoxyethoxyethyl acrylate, ethoxylated phenyl monoacrylate, hydroxyethyl acrylate, hydroxypropyl acrylate, hydroxybutyl acrylate, isooctyl acrylate, n-butyl acrylate, isobutyl acrylate, neopentyl glycol diacrylate, ethylene glycol diacrylate, diethylene glycol diacrylate, dipropylene glycol diacrylate, triethylene glycol diacrylate, tetraethylene glycol diacrylate, 1,6-hexane diol diacrylate, tripropylene glycol diacrylate, glycerol triacrylate, trimethylol propane diacrylate, trimethylol propane triacrylate, pentaerythritol tetraacrylate, phenoxyethyl acrylate, methyl methacrylate, ethyl methacrylate, propyl methacrylate, n-butyl methacrylate, isobutyl methacrylate, hydroxyethyl methacrylate, hydroxypropyl methacrylate, cyclohexyl methacrylate, glycerol mono-methacrylate, glycerol 1,3-dimethacrylate, trimethylcyclohexyl methacrylate, methyl triglycol methacrylate, isobornyl methacrylate, trimethylolpropane trimethacrylate, neopentyl glycol dimethacrylate, ethylene glycol dimethacrylate, diethylene glycol dimethacrylate, 1,6- hexanediol dimethacrylate, hydroxybutyl methacrylate, tetrahydrofurfuryl methacrylate, phenoxyethyl methacrylate, polyethylene glycol dimethacrylate and so forth. Other (meth)acrylate compounds which may be included in the inventive compositions include polyethylene glycol di(meth)acrylates, bisphenol-A di(meth)acrylates, such as ethoxylated bisphenol-A methacrylate ("EBIPMA") and tetrahydrofuran (meth)acrylates and di(meth)acrylates, ethoxylated trimethylol propane tri(meth)acrylates, (meth)acrylated polyesters, (meth)acrylated polyethers, (meth)acrylate capped urethane compounds and combinations thereof.

Further monomers, prepolymer and oligomer compounds having olefinically unsaturated functional groups co-curable with (meth)acrylate compounds, for instance vinyl acylate monomers, diene monomers, stryryl functional monomers, (meth)acrylamido functional monomers, corresponding prepolymer compounds and oligomers, and the like, may also be included in the compositions of the invention.

The curable compositions may be coating, adhesive or sealant compositions. Many such formulations are commercially available or described in the art, and may be beneficially modified by inclusion of the inventive monomer compositions.

The curable compositions are suitably formulated with a free radical initiator, although in some cases they may be curable, e.g. by irradiation without including an initiator compound.

For compositions which are desired to be photocuring a photoinitiator component will typically be included. The photoinitiators are suitably active in the UV/visible range, approximately 250–850 nm, or some segment thereof. Examples of photoinitiators, which initiate under a free radical mechanism, include benzophenone, acetophenone, chlorinated acetophenone, dialkoxyacetophenones, dialkylhydroxyacetophenones, dialkylhydroxyacetophenone esters, benzoin, benzoin acetate, benzoin alkyl ethers, dimethoxybenzoin, dibenzylketone, benzoylcyclohexanol and other aromatic ketones, acyloxime esters, acylphosphine oxides, acylphosphonates, ketosulfides, dibenzoyldisulphides, diphenyldithiocarbonate and diphenyl(2,4,6-trimethylbenzoyl) phosphine oxide. The photoinitiators that may be used in the adhesive compositions of the present invention include photoinitiators available commercially from Ciba-Geigy Corp., Tarrytown, N.Y. under the "IRGACURE" and "DAROCUR" tradenames, specifically "IRGACURE" 184 (1-hydroxycyclohexyl phenyl ketone), 907 (2-methyl-1-[4-(methylthio)phenyl]-2-morpholino propan-1-one), 369 (2-benzyl-2-N,N-dimethylamino-1-(4-morpholinophenyl)-1-butanone), 500 (the combination of 1-hydroxy cyclohexyl phenyl ketone and benzophenone), 651 (2,2-dimethoxy-2-phenyl acetophenone), 1700 (the combination of bis(2,6-dimethoxybenzoyl-2,4-,4-trimethyl pentyl phosphine oxide and 2-hydroxy-2-methyl- 1-phenyl-propan-1-one) and "DAROCUR" 1173 (2-hydroxy-2-methyl-1-phenyl-1-propane) and 4265 (the combination of 2,4,6-trimethylbenzoyldiphenyl-phosphine oxide and 2-hydroxy-2-methyl-1-phenyl-propan-1-one); photoinitiators available commercially from Union Carbide Chemicals and Plastics Co. Inc., Danbury, Conn. under the "CYRACURE" tradename, such as "CYRACURE" UVI-6974 (mixed triaryl sulfonium hexafluoroantimonate salts) and UVI-6990 (mixed triaryl sulfonium hexafluorophosphate salts); and the visible light [blue] photoinitiators, d1-camphorquinone and "IRGACURE" 784DC. Of course, combinations of these materials may also be employed herein.

Photoinitiators particularly suitable for use herein include ultraviolet photoinitiators, such as 2,2-dimethoxy-2-phenyl acetophenone (e.g., "IRGACURE" 651), and 2-hydroxy-2-methyl-1-phenyl-1-propane (e.g., "DAROCUR" 1173) and the ultraviolet/visible photoinitiator combination of bis(2,6-dimethoxybenzoyl-2,4,4-trimethylpentyl) phosphine oxide and 2-hydroxy-2-methyl-1-phenyl-propan-1-one (e.g., "IRGACURE" 1700), as well as the visible photoinitiator bis($\eta^5$-2,4-cyclopentadien-1-yl)-bis[2,6-difluoro-3-(1H-pyrrol-1-yl)phenyl]titanium (e.g., "IRGACURE" 784DC). "LUCIRIN" TPO, from BASF is another preferred photoinitiator.

Typically, the photoinitiators will be employed in an amount of 0.1 to 10%, suitably 0.5 to 7% and especially from about 1 to about 5% by weight of the composition.

The photocuring compositions of the invention may be cured by transmitting energy to the composition which is effective to activate the photoinitiator, suitably by irradiation, typically with UV or visible light. Irradiation of substrates treated in accordance with the practice of the invention can be achieved by the use of UV lamps such as mercury arc lamps (high, medium and low pressure), xenon arc lamps, high intensity halogen-tungsten arc lamps, microwave driven arc lamps and lasers. Additional means of irradiation which can be used are, for example, x-rays, ionizing irradiation using $^{60}$Co γ-rays and electron beam irradiation. In some cases the compositions may also be curable by heat or by IR irradiation.

Additionally or alternatively to a photoinitiator, the curable formulations of the present invention may include a peroxide, azonitrile or other thermally activated free-radical initiator, including within this category anaerobically curing ambient temperature initiator systems which are well known in the art of curable (meth)acrylate compositions. Typical curing agents are hydroperoxides, for example, t-butyl hydroperoxide, p-methane hydroperoxide, cumene hydroperoxide, diisopropylbenzene hydroperoxide, and the like. Typically, thermally activated initiators will be employed in an amount of 0.1 to 10%, suitably 1 to 5% by weight of the composition.

An accelerator may be included, particularly if the composition is curable by an anaerobic curing mechanism. Typical accelerators include amines, amine oxides, sulfonamides, metal sources, acids and/or triazines, for example, ethanol amine, diethanol amine, triethanol amine, N,N dimethyl aniline, benzene sulphonimide, cyclohexyl amine, triethyl amine, butyl amine, saccharin, N,N-diethyl-p-toluidine, N,N-dimethyl-o-toluidine, acetyl phenylhydrazine, maleic acid and the like. Of course, other materials known to induce anaerobic cure may also be included or substituted therefor. See e.g., U.S. Pat. No. 3,218,305 (Krieble), U.S. Pat. No. 4,180,640 (Melody), U.S. Pat. No. 4,287,330 (Rich) and U.S. Pat. No. 4,321,349 (Rich). Typically, accelerators will be employed in an amount of 0.1 to 10%, suitably 0.5 to 5% by weight of the composition.

The cyclic carbonate group in the inventive compounds provides an additional cross-linking site by an optional secondary cure mechanism. Exemplary of such a secondary mechanism are ring-opening addition reactions with multi-amine and multicarboxylic acid curing agents. The new monomers may also be polymerized through the cyclic carbonate group (with cationic or anionic catalysts) to give acyclic polycarbonates that show little or no shrinkage on polymerization.

To facilitate curing through propylene carbonate polymerization the photoinitiator component may be, or may include, a cationic photoinitiator. Suitable cationic photoinitiators are onium salts represented by the general formula:

where $R^6$ is an aromatic radical, for instance aryl, alkaryl, and aralkyl groups, including fused ring structures comprising an aromatic ring, which may be optionally substituted with a linear, branched or cyclic $C_8$ to $C_{20}$ radical of alkyl, alkylene, alkoxy alkyleneoxy, a nitrogen, oxygen or sulfur heterocyclic radical of 4 to 6 carbon atoms in the ring; or a mixture thereof, $A^+$ is selected from the group of iodonium cation mono-substituted with $C_1$ to $C_{20}$ alkyl or aryl optionally substituted with $C_1$ to $C_{20}$ alkyl or alkoxy and sulfonium cation di-substituted with $C_1$ to $C_{20}$ alkyl or aryl optionally substituted with $C_1$ to $C_{20}$ alkyl or alkoxy or a mixture thereof and X– is a non-basic, non-nucleophilic anion, examples of which include $SbF_6^-$, $AsF_6^-$, $PF_6^-$, $BF_4^-$, $ClO_4^-$, $CF_3SO_3^-$ and the like. Examples of such cationic photoinitiators are diaryliodonium, triarylsulfonium, diaryliodosonium, triarylsulfoxonium, dialkylphenacylsulfonium and alkylhydroxyphenylsulfonium salts. Syntheses of such onium salts are described in U.S. Pat. No. 4,219,654 (Crivello); U.S. Pat. No. 4,058,400 (Crivello); U.S. Pat. No. 4,058,401 (Crivello) and U.S. Pat. No. 5,079,378 (Crivello). Although various members of the series of onium salts indicated above may be used in the practice of this invention, those bearing the $SbF_6^1$ anion are preferred. Commercial aryl onium salt cationic photoinitiators include UVI-6974, from Dow Chemical and UVE 1014 and UVE 1016 from General Electric Co.

Other suitable cationic photoinitiators include $\eta^5,\eta^6$-iron arene complex salt catalysts as described in U.S. Pat. No. 4,808,638 (Steinkraus et al) at cols 5–6. These catalysts, characterized as "ferrocenium salt" catalysts include, for instance IRGACURE 261 [$\eta^5$-2,4-cyclopentadien-1-yl][(1,2,3,4,5,6-$\eta$)(1-methyl ethyl)benzene]-iron (+)-hexafluorophosphate (–), sold by Ciba Speciality Chemicals.

In compositions comprising cationic photoinitiator compounds the inventive monomers may have particular advantage in improving solubility of the cationic photoinitiator component in the overall composition.

In connection with the secondary cure mechanism provided by the inventive monomer compounds, curable compositions of the invention may be formulated with other compounds co-curable the inventive compounds by such secondary cure mechanism. Examples of such other compounds include epoxy, vinyl ether, styryloxy and polythiols.

The compositions of the invention may also include an inhibitor of polymerization in an amount effective to give desired shelf stability to the composition. Suitable inhibitors are well known to those skilled in the art and include those described in the aforementioned patents which described anaerobic compositions. Metal chelators, such as ethylenediamine tetraacetate ("EDTA"), or salts thereof, and 1-hydroxyethylidine-1,1-diphosphonic acid ("HEDPA"), and quinone type inhibitors, such as hydroquinone, methyl hydroquinone, napthoquinone, anthraquinone and benzoquinone, as well as BHT (butylated hydroxy toluene), are exemplary. Such inhibitors are typically employed at a level of 0.1–1.0% by weight of the composition.

Various adhesion promoters may be used in the curable compositions of the invention. Adhesion promoters may include acid functional monomers such as acrylic acid or methacrylic acid, and silane adhesion promoters such as glycidoxypropyltrimethoxysilane, methacryloxypropyltrimethoxysilane, methacryloxypropyltriacetoxysilane, and acryloxypropyltrimethoxysilane, and various unsaturated nitrogen-containing compounds such as N,N'-dimethylacrylamide, acryloyl morpholine, and the adhesion promoters described in International Patent Publication No. WO 00/40663, for instance N-methyl-N-vinyl acetamide, N-vinyl caprolactam, N-vinylphthalimide, Uracil, and N-vinylpyrrolidone. Adhesion promoters may be used alone or in combination. The adhesion promoter or promoters may suitably be employed in the curable formulations in an amount from about 0.5% to about 30% by weight of the composition, more typically 1% to about 20% by weight, and particularly about 2% to about 10% by weight.

The compositions of the invention may also include an elastomeric polymer toughener, or mixture thereof. The toughening polymer will typically, but always be a block copolymer, including terpolymer, with a Tg of one block segment below –20° C. Suitably the elastomeric polymer is one which is dissolvable or highly swellable in the vinyl ether or propenyl ether monomer utilized in the formulation. Examples of suitable polymer tougheners include acrylic rubbers, butadiene/acrylonitrile rubber, styrene/butadiene rubber, buna rubber, polyisobutylene, polyisoprene, natural rubber, polyurethane rubbers, ethylenevinyl acetate polymers, fluorinated rubbers, isoprene-acrylonitrile polymers, chlorosulfonated polyethylenes, homopolymers of polyvinyl acetate, etc. Preferred polymer tougheners include acrylic rubbers and millable polyurethane rubbers.

The amount of toughener can be varied to suit particular applications. A high level of toughener increases the viscosity of the resulting composition. The concentration range of elastomeric polymer will suitably be from about 3 to about 50 percent by weight, preferably 5 to about 30 percent, and more preferably about 7 to about 25% based on the weight of the composition. Mixtures of tougheners can be used if desired.

In addition to the composition components described above, the compositions may also include non-elastomeric polymers such as poly(methyl methacrylate), polystyrene, poly-α-methylstyrene, polyacenaphthalene, polyindene, polyphenols, and novolac resins. Inorganic fillers such as silica, talc, clay, barytes, hydrated alumina and glass, polyolefin or polyimide fibers may also be included to provide desirable mechanical characteristics, provided that they are not supplied in sufficient amount to preclude sufficient light penetration to the desired cure depth to effect cure initiation within a reasonable irradiation time.

The inventive compositions may also optionally contain other conventional additives e.g. to regulate storage stability, viscosity, surface wetting properties, to promote adhesion, and the like. The formulation may be provided with a colorant, fluorescent agent or phosphorescent agent, for instance, to facilitate inspection of the applied composition prior to curing.

Examples specific applications where the inventive monomers provide beneficial results include as diluents in photocurable DVD bonding formulations, panel-bonding formulations and specialty coatings, and in electronics as a precursor of latent fluxing agents and for high-dielectric coatings.

The invention is illustrated by the following non-limiting examples.

EXAMPLE 1

Synthesis of 1-(Propyleneoxy Carbonate)propyl Acrylate

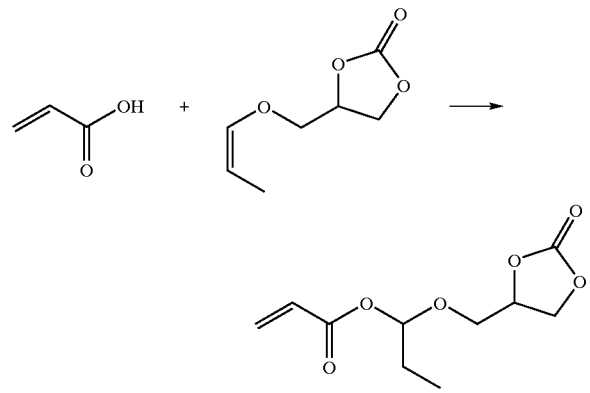

To a 500 mL reaction flask equipped with a heating mantel, mechanical stirrer and addition funnel was added 4-(1-propenyloxymethyl)-1,3-dioxolan-2-one (158 g; 1.0 moles) and 4-tert-butylcatechol (0.266 g;). The mixture was stirred, heated to 80° C. at which time acrylic acid (126 g; 1.75 moles) was added dropwise over about 30 minutes. After the addition was complete the mixture was heated and stirred for an additional 11 hours at 80° C. After cooling, the crude product was transferred to a separating funnel and extracted with a saturated solution of sodium bicarbonate (2×300 mL) to remove residual acrylic acid. The acid free solution was washed with water (300 mL) and dried over magnesium sulfate. The solution was filtered to give the carbonate functionalized acrylate monomer as a light yellow colored liquid (194 g; 84% yield). The structure of the product was confirmed by spectral analysis: $^1$H NMR (CDCl3); δ 5.9–6.5, m, 4H, $CH_2$=CH— and O—CH(Et)—O; δ 4.8, m, 1H, —$CH_2$—CH—O; δ 3.8–4.6, m, 4H, —$CH_2$—O; 6 1.8, m 2H, —$CH_2$—$CH_3$; δ 1.0, t, 3H, —$CH_2$—$CH_3$; IR (ATR film); 1800 and 1720 $cm^{-1}$, carbonyl group of carbonate; 1635 $cm^{-1}$, acrylate double bond.

EXAMPLE 2

UV-curable Formulations Containing 1-(propyleneoxy carbonate)propyl Acrylate (PCPA) and N,N-Dimethylacrylamide (N,N-DMA)

N,N-DMA is frequently used in UV-curable formulations as a reactive monomer to enhance curing rates and provide tack-free surfaces when the formulations are cured in air. In this experiment the comparative performance of N,N-DMA and PCPA to promote surface curing in a UV-initiated acrylate composition was measured. UV-curable formulations containing the carbonate acrylate monomer PCPA, synthesized as described in Example 1 (formulation A), and N,N-DMA (formulation B) were prepared by blending together the components listed in Table 1.

TABLE 1

UV-curable formulations A and B. All amounts are % by weight

| Component | A | B (Comp.) |
|---|---|---|
| PCPA (example 1) | 24.3 | 0 |
| N,N-DMA | 0 | 24.3 |
| Isobornyl acrylate | 39.3 | 39.3 |
| Urethane-acrylate resin I | 31.4 | 31.4 |
| Adhesion promoter | 1.5 | 1.5 |
| IRGACURE 651* | 2.5 | 2.5 |
| LUCIRIN TPO* | 1.0 | 1.0 |

*photoinitiator

Coatings of each formulation, about 0.5 mm in film thickness, were prepared on microscope glass slides and exposed to UV light from a Zeta 7200 lamp to cure the coatings (incident intensity 50 mW/cm$^2$, 365 nm). The minimum exposure time needed to obtain a tack-free surface was determined by brushing the surface of the exposed film in the presence of silicon carbide grit. The tack-free time was determined as the exposure time required to produce a film with no significant amounts of residual grit. The results are presented in Table 2.

TABLE 2

Tack-free surface times for formulations A and B

| Formulation | Tack-free time (minutes) |
|---|---|
| A | 1 |
| B | >3 |

The result shows that PCPA is superior to N,N-DMA in promoting surface cure in UV-acrylate systems.

EXAMPLE 3

Comparative Performance of PCPA and Isobornyl Acrylate

An experiment, similar to that of Example 2 was performed to compare the performance of PCPA and isobornyl acrylate as reactive diluents in UV-curable compositions. The formulations are described in Table 3.

TABLE 3

UV-curable formulations C and D. All amounts are % by weight

| Component | C | D (Comp.) |
|---|---|---|
| PCPA (example 1) | 42.2 | 0 |
| Isobornyl acrylate | 0 | 42.2 |
| Urethane-acrylate resin II | 48.6 | 48.6 |
| Acrylic acid | 1.5 | 1.5 |
| Adhesion promoter | 0.6 | 0.6 |
| IRGACURE 184* | 2.0 | 2.0 |

*photoinitiator

Coatings of each formulation of each formulation were prepared and cured as described in Example 2. The results are presented in Table 4.

TABLE 4

Tack-free surface times for formulations C and D

| Formulation | Tack-free time (seconds) |
|---|---|
| C | 15 |
| D | 60 |

The result shows that PCPA is superior to isobornyl acrylate in promoting surface cure in UV-acrylate systems.

EXAMPLE 4

Surface Curing Rates Determined by Infrared (IR) spectroscopy

The surface curing rates of formulation A (Example 2) was determined by IR analysis in attenuated total reflectance mode (ATR). The coating was exposed to UV light under the conditions of Example 2 and then placed on the ATR crystal of the IR spectrophotometer with the top surface of the coating in contact with the ATR crystal surface. An infrared spectrum of the surface layer (the top 2 μm layer of the cured film) was obtained in this manner. The disappearance of the of the absorption bands associated with the acrylate double bonds at 1636 and 1618 cm$^{-1}$ in the IR spectrum are indicative of the conversion of monomers to cured polymer. Coatings of the formulation were exposed to UV light for various time and individual IR spectra recorded. The results are shown in FIG. 1, an ATR-IR transmission spectra of formulation A.

Line A in FIG. 1 is the IR spectra of the uncured formulation before exposure to UV light. Line B is the IR spectra obtained after 5 seconds exposure. After 5 seconds exposure the acrylate double bond absorption bands have completely disappeared indicating that monomer conversion is essentially complete in this time.

The occurrence of tacky surface layers in UV-cured acrylate coatings is the result of inhibition of inhibition of the photo initiated polymerization reaction by atmospheric oxygen, which diffuses into the surface layers at rates sufficient to quench the polymerization process. The formation of tack-free surfaces in formulations containing PCPA can therefore be attributed to the extremely rapid rates of acrylate group conversion, which occur at rates sufficiently high to prevent oxygen diffusion from inhibiting the polymerization reaction.

EXAMPLE 5

Synthesis of 3-(2-Vinyloxyethoxy)propylene-1,2-carbonate and its Corresponding Hemiacetal Acrylate by Reaction with Acrylic Acid

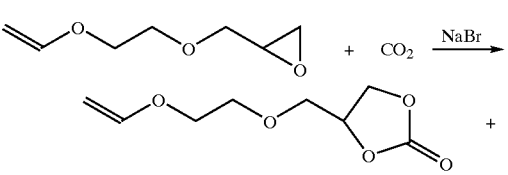

-continued

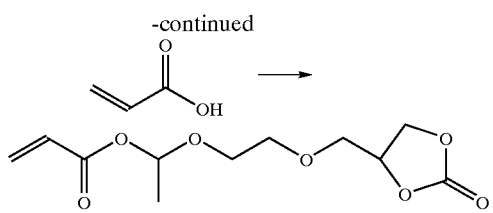

Fifty grams of 2-vinyloxyethyl glycidyl ether (VEGE, 0.35 mol) was dissolved in 150 mL of N-methyl pyrrolidinone along with 3.6 g sodium bromide (0.035 mol, 0.1 eq). The mixture was warmed to 100° C. and carbon dioxide was bubbled through the mixture. (A glass adapter and plastic tube was fitted to a flask partially filled with dry ice. A glass pipet attached to the other end of the plastic tubing was placed just under the surface of the reaction mixture.) After two hours, NMR and GC analyses of the reaction mixture indicated that the epoxy had been completely converted to carbonate. The mixture was concentrated under rotary evaporation (0.2 Torr, 68° C.). The mixture was washed with water three times to remove residual solvent and sodium bromide; GC analysis showed that no solvent remained.

The water washings were combined and shaken with about 200 mL of ethyl acetate to extract that fraction of desired product that had partitioned to the aqueous layer. The ethyl acetate was then washed with water to remove NMP solvent that had co-extracted along with the desired product. The ethyl acetate was dried twice over magnesium and sodium sulfates, filtered, and concentrated by rotary evaporation. A total of 44.5 g of the intermediate product, 3-(2-vinyloxyethoxy)propylene-1,2-carbonate, was obtained for a 68 percent yield.

The 3-(2-vinyloxyethoxy)propylene-1,2-carbonate product (12 g, 0.06 mol) was added to a 50 mL flask. Acrylic acid (1.7 g, 0.24 mol) was added and the mixture was warmed gently and an exotherm to 83° C. was noted. Another 3.4 g of acrylic acid was added dropwise (total of 0.071 mol, 1.1 eq). The mixture was heated to 80° C. briefly. An NMR spectrum of the crude reaction mixture showed that all vinyl ether groups had been consumed and that the desired the acrylated hemiacetal carbonate product was present in the mixture.

EXAMPLE 6

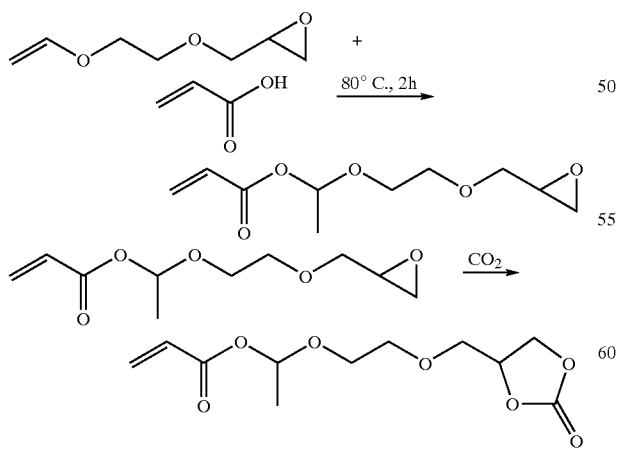

The product of Example 5 can also be prepared by reversing the sequence of reactions described above. Thus an equimolar solution of VEGE and acrylic acid is heated at 80° C. for several hours to give intermediate product 1-acryloxy-1-(2-glycidoxy)ethoxy ethane in high yield. The mixture is washed with sodium bicarbonate to neutralize residual acid, then washed with water, dried over magnesium sulfate and filtered. The product is dissolved in N-methyl pyrrolidinone and 0.1 eq of sodium bromide is added. The mixture is warmed to 100° C. and carbon dioxide is bubbled through the mixture for two hours. The mixture is concentrated by rotary evaporation to remove the bulk of the solvent. The mixture is washed with water to remove residual NMP and sodium bromide, then dried over magnesium sulfate and filtered to yield a product comprising the acrylated hemiacetal carbonate monomer

What is claimed is:

1. A compound of the formula:

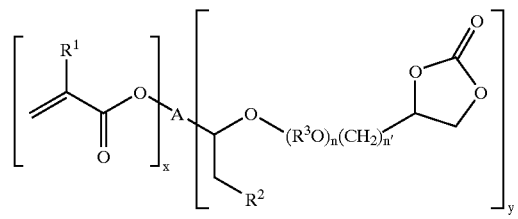

wherein $R_1$ is H or methyl, $R^2$ is H or alkyl, $R^3$ is $C_2$–$C_4$ alkylene, n is 0–4, n' is 1–4, x is one or more, y is one or more, x+y=z, and A is a z-valent organic group linked to the group or groups on the left thereof through a carbon atom and is linked to the group or groups on the right thereof through an ether or ester oxygen atom, or, provided that x and y are both 1, a direct bond.

2. A compound as in claim 1 wherein the organic group A is linked to the group or groups on the right thereof through an ether oxygen atom.

3. A compound as in claim 1 wherein the organic group A is linked to the group or groups on the right thereof through an ester oxygen atom.

4. A compound as in claim 1 wherein z is 2–6.

5. A compound as in claim 1 wherein x and y are both 1.

6. A compound as in claim 1 wherein A is a direct bond.

7. A compound as in claim 5 wherein A is an alkyleneoxide group, or an alkyleneacetyloxy group.

8. A compound as in claim 1 selected from the group consisting of compounds of the formulae:

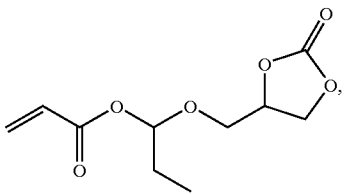

-continued

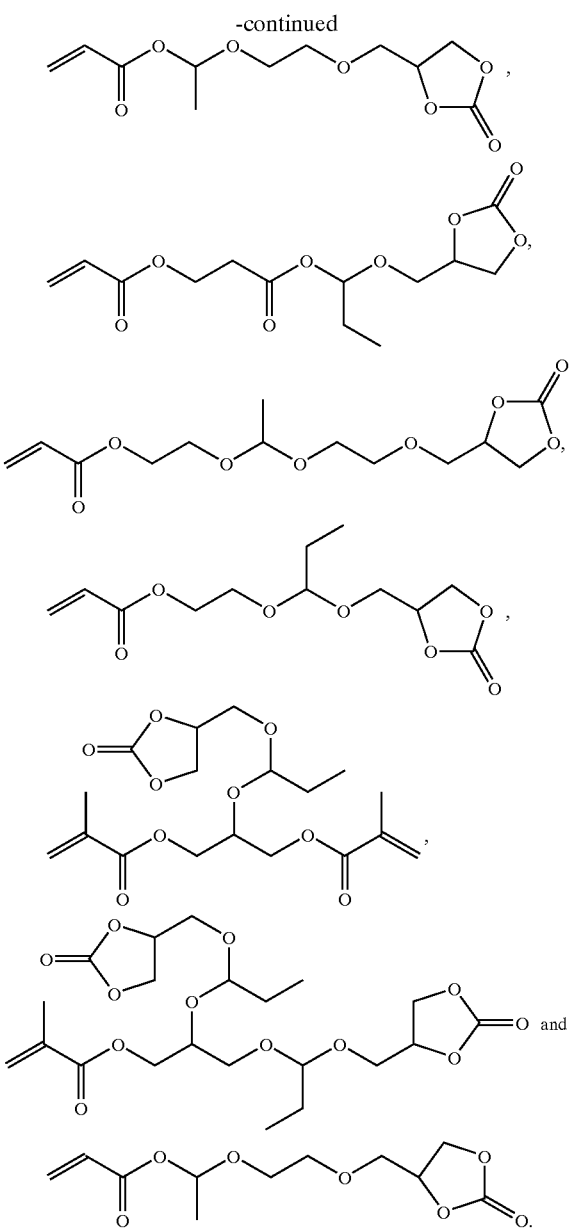

9. A curable composition comprising a compound as in claim 1 as a first component and second component, said second component having a chemical structure different from the first component and being co-curable with said first component by a free-radical or cationic polymerization mechanism.

10. A curable composition as in claim 9 wherein the second component is an olefinically unsaturated free-radically polymerizable compound.

11. A curable composition as in claim 10 wherein the second component is a compound of the formula: $(H_2C=CR^4C(=O)Q)_nR^5$, wherein $R^4$ is hydrogen, halogen or alkyl of 1 to about 4 carbon atoms, Q is O, NH or $NCH_3$, n is a positive number of at least 1 and $R^5$ is an n-valent organic group.

12. A curable composition as in claim 10 wherein second component is a (meth)acrylate functional compound.

13. A curable composition as in claim 9 wherein the second component is a cationically polymerizable compound.

14. A curable composition as in claim 9 further comprising a free radical initiator.

15. A curable composition as in claim 14 wherein the free radical initiator is a free radical photoinitiator.

16. A curable composition as in claim 9 further comprising a cationic photoinitiator.

17. A curable composition comprising a compound as in claim 1 and a free radical or cationic photoinitiator.

18. A curable composition comprising a compound as in claim 1 and a multi-amine or a multicarboxylic acid.

19. A curable composition comprising a compound as in claim 1 and a thermally activated free-radical initiator.

20. A curable composition comprising a compound as in claim 1 and at least one member selected from the group consisting of an epoxy compound, a vinyl ether, a styryloxy compound, and a polythiol.

21. A method of forming a (meth)acrylate compound comprising reacting together, at a temperature above ambient and in the presence of a thermal stabilizer, an alk-1-enyl alkylene cyclocarbonate ether of the formula:

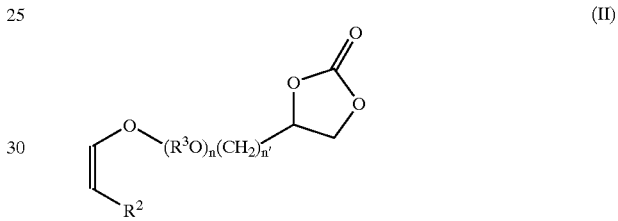

(II)

wherein
$R^2$ is H or alkyl
$R^3$ is $C_{2-C4}$ alkylene,
n is 0–4, and
n' is 1–4,
with a (meth)acrylic carboxylic acid or a hydroxy functional (meth)acrylic ester.

22. A method as in claim 21 wherein $R^2$ is H, or an alkyl group of 1–10 carbon atoms; and the $R^3$ groups are selected from ethylene, 1,2-propylene, 1,3-propylene, 1,4-butylene and 1,2-butylene.

23. A method as in claim 21 wherein the alk-1-enyl alkylene cyclocarbonate ether compound is prop-1-enyl propylene carbonate (PEPC), or the vinyloxyethyl ether of propylene carbonate.

24. A method as in claim 21 wherein the alk-1-enyl alkylene cyclocarbonate ether is reacted with a (meth)acrylic carboxylic acid.

25. A method as in claim 24 wherein the (meth)acrylic carboxylic acid is a member selected from the group consisting of acrylic acid, methacrylic acid, β-carboxyethyl acrylate and β-carboxyethyl methacrylate.

26. A method as in claim 21 wherein the alk-1-enyl alkylene cyclocarbonate ether is reacted with a (meth)acrylic hydroxy ester.

27. A method as in claim 26 wherein the (meth)acrylic hydroxy ester is a partially (meth)acrylated diol or polyol.

28. A method as in claim 26 wherein the (meth)acrylic hydroxy ester is a member of the group consisting of hydroxyethyl acrylate, hydroxyethyl methacrylate, hydroxypropyl acrylate, hydroxypropyl methacrylate, glyceryl monomethacrylate, glyceryl monoacrylate, glyceryl dimethacrylate, glyceryl diacrylate, trimethylol propane monomethacrylate, trimethylol propane monomethacrylate, trimethylol diacrylate, trimethylol propane dimethacrylate; pentaerythritol tri(meth)acrylate, pentaerythritol di(meth)acrylate, pentaerythritol mono(meth)acrylate, sorbitol penta(meth)acrylate, sorbitol tetra(meth)acrylate, sorbitol tri(meth)acrylate, sorbitol di(meth)acrylate, sorbitol mono(meth)acrylate, hydroxy functional saccharide (meth)acrylates, diethylene glycol mono(meth)acrylate, poly(ethylene glycol) mono(meth)acrylate, dipropylene glycol mono(meth)acrylate; and poly(propylene glycol) mono(meth)acrylate.

29. A method of forming a (meth)acrylate compound, a step of which comprises reacting together, at a temperature above ambient and in the presence of a thermal stabilizer, an alk-1-enyl alkylene epoxy ether of the formula:

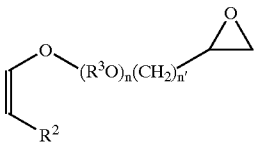

(II)

wherein
  $R^2$ is H or alkyl
  $R^3$ is $C_2$–$C_4$ alkylene,
  n is 0–4, and
  n' is 1–4,
with a (meth)acrylic carboxylic acid or a hydroxy functional (meth)acrylic ester, and then reacting the resulting acetal, or hemiacetal ester, linked epoxide with carbon dioxide.

* * * * *